(12) United States Patent
Kersey (10) Patent No.: US 11,324,425 B2
(45) Date of Patent: May 10, 2022

(54) APPARATUS AND METHOD FOR ASSESSMENT OF CANCER MARGIN

(71) Applicant: Alan D. Kersey, South Glastonbury, CT (US)

(72) Inventor: Alan D. Kersey, South Glastonbury, CT (US)

( * ) Notice: Subject to any disclaimer, the term of this patent is extended or adjusted under 35 U.S.C. 154(b) by 0 days.

(21) Appl. No.: 17/073,611

(22) Filed: Oct. 19, 2020

(65) Prior Publication Data

US 2021/0128026 A1 May 6, 2021

Related U.S. Application Data

(62) Division of application No. 16/202,852, filed on Nov. 28, 2018, now abandoned.
(Continued)

(51) Int. Cl.
*A61B 5/1459* (2006.01)
*A61B 1/00* (2006.01)
(Continued)

(52) U.S. Cl.
CPC .......... *A61B 5/1459* (2013.01); *A61B 1/0017* (2013.01); *A61B 5/0075* (2013.01);
(Continued)

(58) Field of Classification Search
CPC . A61B 5/1459; A61B 5/14546; A61B 1/0017; A61B 5/0075; A61B 5/0084;
(Continued)

(56) References Cited

U.S. PATENT DOCUMENTS

| 4,200,110 A | 4/1980 | Peterson et al. |
| 4,560,248 A * | 12/1985 | Cramp ............... G01N 21/7703 356/402 |

(Continued)

FOREIGN PATENT DOCUMENTS

| CN | 106716137 A * | 5/2017 | ......... G01N 33/4915 |
| JP | 4290367 B2 * | 7/2009 | ............. G01N 21/49 |

(Continued)

OTHER PUBLICATIONS

Nguyen and Tsien, "Fluorescence-guided surgery with live molecular navigation—a new cutting edge", Nat Rev Dancer, vol. 13(9), Sep. 2013, pp. 653-662, 2013 Macmillan Publishers Limited.
(Continued)

*Primary Examiner* — Mohamed K Amara
(74) *Attorney, Agent, or Firm* — Ware, Fressola, Maguire & Barber LLP (57) ABSTRACT

An apparatus for inspecting a biological tissue uses a pH-sensitive coating material to determine whether the tissue is normal or cancerous. The coating material is placed in contact with the tissue to be excited by an excitation light. The coating material is arranged to provide a response signal indicative of the pH value of the tissue. Using a fiber bundle having a plurality of optical fibers forming a linear array or a two-dimensional array adjacent the coating material, the imaging of localized surface pH in the biological tissue can be achieved using the response signal through each of the optical fibers. The fiber bundle can be arranged as a probe to examine the tissue for providing direct mapping of the tumor margin via a display, so that a surgeon can inspect the tissue in real-time.

21 Claims, 10 Drawing Sheets

Related U.S. Application Data (60) Provisional application No. 62/591,335, filed on Nov. 28, 2017.

(51) Int. Cl.
| | |
|---|---|
| *A61B 5/00* | (2006.01) |
| *A61B 5/145* | (2006.01) |
| *G01N 33/574* | (2006.01) |
| *G01N 33/483* | (2006.01) |
| *G01J 3/44* | (2006.01) |
| *G01N 21/27* | (2006.01) |
| *G01N 21/65* | (2006.01) |

(52) U.S. Cl.
CPC ........ *A61B 5/0084* (2013.01); *A61B 5/14539* (2013.01); *A61B 5/14546* (2013.01); *G01N 33/4833* (2013.01); *G01N 33/574* (2013.01); *A61B 1/00167* (2013.01); *G01J 3/44* (2013.01); *G01J 2003/4424* (2013.01); *G01N 21/274* (2013.01); *G01N 21/65* (2013.01)

(58) Field of Classification Search
CPC ............ A61B 5/14539; A61B 1/00167; G01N 33/4833; G01N 33/574; G01N 21/274; G01N 21/65; G01N 21/80; G01N 31/221; G01J 3/44; G01J 2003/4424; G02B 2006/0325; G02B 6/02042; H01S 3/06708; H01S 3/06741; H01S 3/169
See application file for complete search history.

(56) References Cited

U.S. PATENT DOCUMENTS

| | | | |
|---|---|---|---|
| 4,785,814 A | 11/1988 | Kane | |
| 4,999,306 A | 3/1991 | Yafuso | |
| 5,047,627 A | 9/1991 | Yim | |
| 5,119,463 A * | 6/1992 | Vurek ................. | G01N 21/7703 422/82.07 |
| 5,320,814 A | 6/1994 | Walt et al. | |
| 5,352,352 A * | 10/1994 | Tsukada ............. | A61B 5/14539 204/414 |
| 5,489,988 A * | 2/1996 | Ackley ................ | G01N 21/783 250/227.11 |
| 5,747,349 A * | 5/1998 | van den Engh ..... | G01N 31/223 436/103 |
| 5,813,403 A | 9/1998 | Soller et al. | |
| 6,040,191 A * | 3/2000 | Grow .................... | G01N 21/65 436/172 |
| 6,162,646 A * | 12/2000 | Webster ................ | G01N 21/80 436/166 |
| 6,200,737 B1 * | 3/2001 | Walt ......................... | G02B 6/06 422/82.06 |
| 6,436,717 B1 | 8/2002 | Wu | |
| 6,454,945 B1 * | 9/2002 | Weigl ................ | B01D 11/0492 204/600 |
| 6,956,995 B1 * | 10/2005 | Shafaat ................... | G02B 6/32 385/33 |
| 6,989,897 B2 * | 1/2006 | Chan .................... | G01N 21/658 356/244 |
| 7,054,513 B2 | 5/2006 | Herz et al. | |
| 7,226,414 B2 | 6/2007 | Ballerstadt | |
| 7,236,812 B1 | 6/2007 | Ballerstadt | |
| 7,419,483 B2 * | 9/2008 | Shehada .............. | A61B 5/0075 604/543 |
| 7,824,925 B2 * | 11/2010 | Wohlstadter ........... | G01N 21/76 436/805 |
| 7,835,003 B2 | 11/2010 | Jiang et al. | |
| 8,328,420 B2 | 12/2012 | Abreu | |
| 8,647,861 B2 * | 2/2014 | Ingber ................ | B01L 3/50273 506/10 |
| 8,849,379 B2 | 9/2014 | Abreu | |
| 8,951,377 B2 | 2/2015 | Say | |
| 9,155,471 B2 | 10/2015 | Lee et al. | |
| 9,207,398 B2 | 12/2015 | Gibson | |
| 9,511,152 B2 | 12/2016 | Gao et al. | |
| 9,848,815 B2 | 12/2017 | Abreu | |
| 2002/0049389 A1 | 4/2002 | Abreu | |
| 2004/0102722 A1 | 5/2004 | Naghavi | |
| 2004/0180391 A1 * | 9/2004 | Gratzl .................... | A61B 5/686 435/14 |
| 2005/0221276 A1 * | 10/2005 | Rozakis ................ | C12Q 1/001 435/4 |
| 2007/0003205 A1 | 1/2007 | Saravanos et al. | |
| 2007/0092975 A1 * | 4/2007 | Potyrailo ............... | G01N 21/78 436/169 |
| 2008/0064942 A1 * | 3/2008 | Gisiger ................ | A61B 5/1477 600/354 |
| 2011/0059016 A1 | 3/2011 | Ramanujam et al. | |
| 2013/0253333 A1 | 9/2013 | Hayman et al. | |
| 2014/0010501 A1 * | 1/2014 | Saito .................... | G02B 6/2551 156/182 |
| 2014/0276103 A1 | 9/2014 | Lee et al. | |
| 2016/0069810 A1 | 3/2016 | Walavalkar et al. | |
| 2017/0015964 A1 * | 1/2017 | Agabi .................... | C12M 23/34 |
| 2018/0045675 A1 * | 2/2018 | Ozel ...................... | G01N 21/80 |
| 2019/0277766 A1 * | 9/2019 | Matousek .............. | G01N 21/65 |

FOREIGN PATENT DOCUMENTS

| | | | | |
|---|---|---|---|---|
| WO | WO-9428452 A1 * | 12/1994 | ............ | G01P 15/093 |
| WO | WO-9739338 A1 * | 10/1997 | ............ | B01F 5/0403 |
| WO | WO-0110881 A1 * | 2/2001 | ............ | C07H 17/075 |
| WO | WO-2012060563 A2 * | 5/2012 | ............ | G21C 17/022 |
| WO | 2017132727 A1 | 8/2017 | | |

OTHER PUBLICATIONS

Tummers, et al., "Real-time Intraoperative Detection of Breast Cancer using Near-Infrared Fluorescence Imaging and Methylene Blue", Eur J Surg Oncol., vol. 40(7), Jul. 2014, pp. 850-858, 2014 Elsevier Ltd.

Dhar et al., "A diffuse reflectance spectral imaging system for tumor margin assessment using custom annular photodiode arrays", Biomedical Optics Express, vol. 3, No. 12, Sep. 27, 2012, 2012 Optical Society of America.

Harmsen et al., "Cancer imaging using Surface-Enhanced Resonance Raman Scattering (SERRS) nanoparticles", Nat Protoc., vol. 12(7), Jul. 2017, pp. 1400-1414.

Yaroslavsky, et al., "Delineating nonmelanoma skin cancer margins using terahertz and optical imaging", J of Biomedical Photonics & Eng , 3(1), Mar. 29, 2017.

Zhang et al., "Nondestructive tissue analysis for ex vivo and in vivo cancer diagnosis using a handheld mass spectrometry system", Science Translational Medicine, vol. 9 (406), Sep. 6, 2017.

Warburg, 0., "On the Origin of Cancer Cells", Science vol. 123, No. 3191, Feb. 24, 1956, pp. 309-314.

Gatenby et al., "Why Do Cancers Have High Aerobic Glycolysis?", Nature Reviews Cancer, vol. 4, Nov. 2004, pp. 891-899.

Webb et al., "Dysregulated pH: a perfect storm for cancer progression", Nature Reviews. Cancer, vol. 11, Sep. 2011, 671-677, 2011 Macmillan Publisher Limited.

Andreev, et al., "pH-sensitive membrane peptides (pHLIPs) as a novel class of delivery agents", Molecular. Membrane Biology, 27(7), Oct. 2010, pp. 341-352, 2010 Informa UK, Ltd.

Adochite et al.,"Targeting Breast Tumors with pH (Low) Insertion Peptides", Mol. Pharmaceutics, vol. 11 (8), 2014, pp. 2896-2905, 2014 American Chemical Society.

Weerakkody et al. "Novel pH-Sensitive Cyclic Peptides", Scientific Reports, vol. 6:31322, Aug. 12, 2016, pp. 1-13.

Korzeniowska et al., "Intracellular pH-sensing using core/shell silica nanoparticles", J Biomed Nanotechnol., Vo. 10 (7), Jul. 2014, pp. 1336-1345.

(56) References Cited

OTHER PUBLICATIONS

Goa X., et al., "In vivo cancer targeting and imaging with semiconductor quantum dots", Nature Biotechnology, vol. 22, No. 8, Aug. 2004, pp. 969-976.

Segala, J., et al., Accurate Analysis of Tumor Margins Using a Fluorescent pH Low Insertion Peptide (pHLIP), Int. J. Mol. Sci., 10, Aug. 4, 2009, pp. 3478-3487.

Karabadzhak, A.G., et al., "pHLIP-FIRE, a Cell Insertion-Triggered Fluorescent Probe for Imaging Tumors Demonstrates Targeted Cargo Delivery In Vivo", ACS Chem. Biol. 9, 11, Nov. 21, 2014, pp. 2545-2553.

Demoin, D.W., et al., "PET Imaging of Extracellular pH in Tumors with 64Cu- and 18F-Labeled pHLIP Peptides: A Structure-Activity Optimization Study", Bioconjugate Chem., 27, 2016., pp. 2014-2023.

Tseng, J.C., et al., In Vivo Fluorescent Labeling of Tumor Cells with the HaloTag® Technology, Current Chemical Genomics, 6, Sep. 20, 2012, pp. 48-54.

Gerweck, L. E., and Seetharaman, K., Cellular pH Gradient in Tumor versus Normal Tissue: Potential Exploitation for the Treatment of Cancer, Cancer Res 56., Mar. 15, 1996, pp. 1194-1198.

Song, A., et al., "High-Performance Fiber-Optic pH Microsensors for Practical Physiological Measurements Using a Dual-Emission Sensitive Dye", Analytical.Chemistry, vol. 69 No.5, Mar. 1, 1997, pp. 863-867.

Zhou, K., et al., "Multicolored pH-Tunable and Activeatable Fluorescence Nanoplatform Responsive to Physiologic pH Stimuli", Journal of the American Chemical Society, 134: Jun. 26, 2012, pp. 7803-7811.

Baldini, F., et al., "An extended-range fibre-optic pH sensor", Sensors and Actuators A: Physical, vols. 37-38, Jun.-Aug. 1993, pp. 180-186.

Lehmann, H. et al., "Fiber-optic pH meter using NIR dye", Sensors and Actuators B 29, 1995, pp. 392-400.

Citterio, D. et al., "Dyes for use in integrated optical sensors", Sensors and Actuators B 38-39, 1997, pp. 202-206, 1997.

\* cited by examiner

FIGURE 1. Diagrammatic representation of pH of the micro-environment in cancer tissue FIGURE 2. Prior Art: Fiber Optic pH probe FIGURE 3: Surgical assessment of margin using an Optical Fiber pH Sensing "Line Array" Imager FIGURE 3A. Surgical assessment of margin using an Optical Fiber pH Sensing "Line Array" Imager FIGURE 4: Surgical assessment of margin using an Optical Fiber pH Sensing Array imager FIGURE 4A Surgical assessment of margin using an Optical Fiber pH Sensing Array Imager

FIGURE 4B

FIGURE 5: Surgical assessment of margin using an Optical Fiber pH Sensing Array imager with direct image feedback to the probe head FIGURE 6: Needle biopsy screening device using FO array imager FIGURE 7. Rapid Needle Biopsy Screening

APPARATUS AND METHOD FOR ASSESSMENT OF CANCER MARGIN

CROSS REFERENCE TO RELATED PATENT APPLICATION

This application is a divisional application of, and claims benefit to, co-pending U.S. patent application Ser. No. 16/202,852, filed on Nov. 28, 2018, which itself claims benefit to U.S. Provisional Application No. 62/591,335, filed Nov. 28, 2017, which are both hereby incorporated by reference in their entirety.

FIELD OF THE INVENTION

The present invention relates generally to an apparatus and method for the assessment of cancer margin, and more specifically to the assessment during surgical procedures using a fiber optic pH sensing array with real-time visual mapping.

BACKGROUND

For many decades the reference method for the diagnosis of cancer has been histopathological examination of tissues using conventional microscopy. This process is known as Surgical Pathology. In Surgical Pathology, samples can be produced from surgical procedures (tumor resection), diagnostic biopsies or autopsies. These samples go through a process that includes dissection, fixation, and cutting of tissue into precisely thin slices which are stained for contrast and mounted onto glass slides. The slides are examined by a pathologist under a microscope, and their interpretations of the tissue results in the pathology "read" of the sample.

Current surgical techniques to resect cancer are limited by the lack of a precise method to determine the boundary between normal and cancerous cells in, known as the 'tumor margin', in real time during surgical procedures. As a result, the success of such surgical procedures relies on the experience and judgement of the surgeon to decide on how much tissue to remove around the tumor. As a result, surgeons often perform what is called cavity shaving, which can result in the removal of excessive amounts of healthy tissue. Conversely, many patients do not have the entire tumor removed during the initial surgery and may need a follow up surgery to remove residual cancer tissue. This can be traumatic to the cancer patient, adding stress, resulting in long-term detrimental effects on the patient outcome.

Advanced optical and EM imaging approaches have been reported for the determination of tumor margin.

Nguyen and Tsien, Fluorescence-guided surgery with live molecular navigation—a new cutting edge, Nat Rev Cancer, 13(9), pp. 653-662, 2013; and Tummers, et al., Real-time intraoperative detection of breast cancer using near-infrared fluorescence imaging and methylene blue. Eur J Surg Oncol., 40(7), 850-858, 2014, discloses the use of fluorescence imaging.

Dahr et al., A diffuse reflectance spectral imaging system for tumor margin assessment using custom annular photodiode arrays, Biomedical Optics Express, 3, (12), 2012, discloses the use of near-infrared spectroscopy.

Harmsen et al., Cancer imaging using surface-enhanced resonance Raman scattering nanoparticles, Nat Protoc., 12(7), pp. 1400-1414, 2017, discloses the use of Raman spectroscopy.

Yaroslaysky, et al., Delineating nonmelanoma skin cancer margins using terahertz and optical imaging, J of Biomedical Photonics & Eng., 3(1), 2017, discloses the use of terahertz reflectivity.

Zhang et al., Nondestructive tissue analysis for ex vivo and in vivo cancer diagnosis using a handheld mass spectrometry system, Science Translational Medicine, 9, 2017, discloses the use of mass spectrometry to profile tumor/normal tissue boundaries has been reported. In this methodology, the use of mass spectrometer coupled to a "pen" that allows testing of tumor tissue by determination and differentiation of the metabolic products produced by cancer cells compared to normal tissue.

Figure 1:
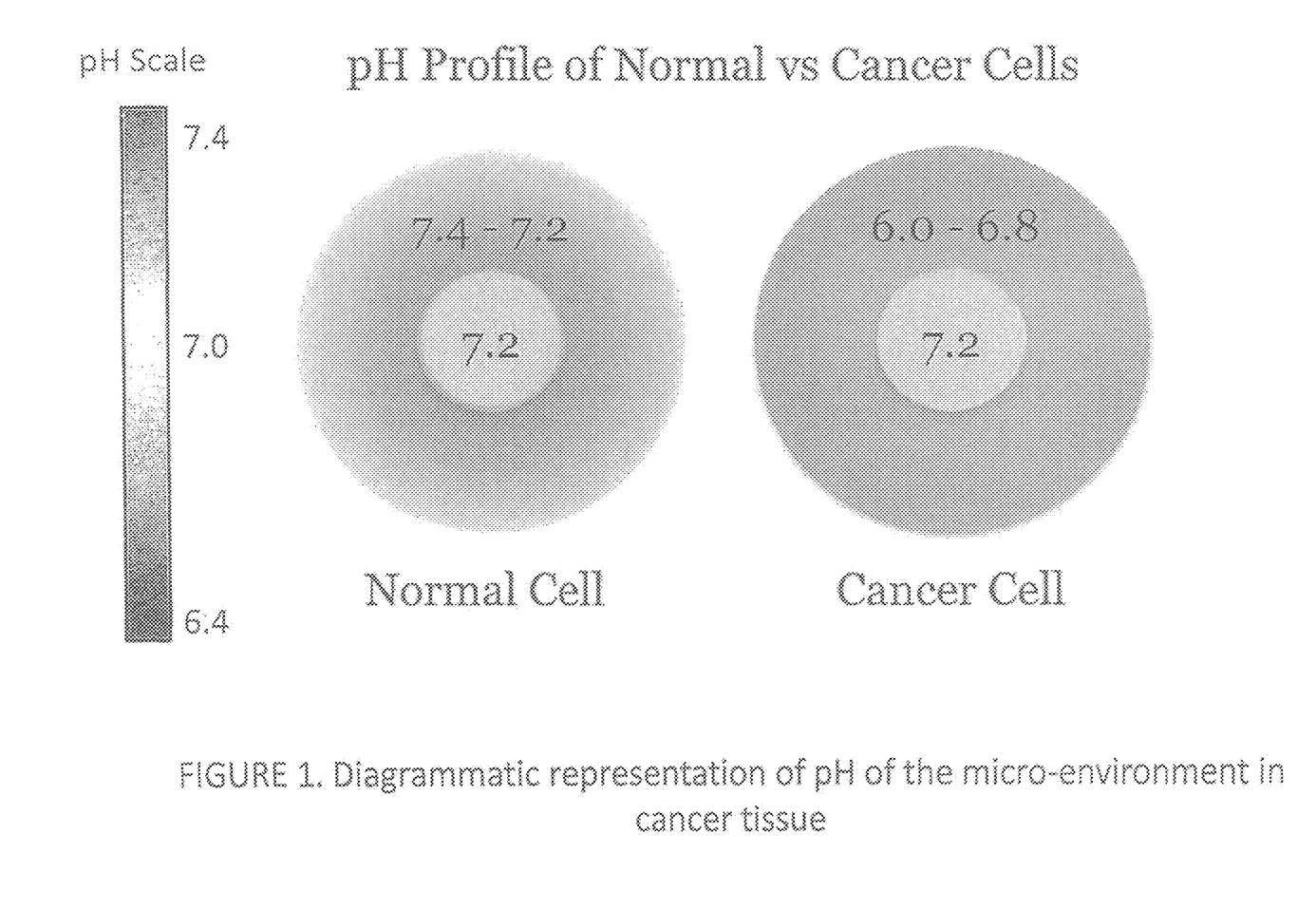
FIG. 1 is a diagrammatic representation of pH of the micro-environment in a cancel cell.

It is known that all tumors exhibit an acidic microenvironment, largely due to the due to glycolytic metabolic processes exhibited by cancer cells: To maintain their rapid growth and proliferation, cancer cells have a higher need for energy which is to a large degree fulfilled by an increased dependence on alternate metabolic pathways. Under aerobic conditions, cancer cells metabolize glucose to lactic acid, a process generally called the Warburg effect (see Warburg, O., On the origin of cancer cells, Science 123, pp. 309-314, 1956). Tumor tissue is also generally hypoxic (lacking in oxygen), has deficient blood perfusion, and has lower glucose levels (Gatenby et al., Why do cancers have high aerobic glycolysis? Nature Rev Cancer, 4, 891, 2004). Generally, this result in a microenvironment is pH of 6.4 to 6.8, whereas the surrounding normal tissue is close to neutral pH (7.2), as illustrated in FIG. 1. The extracellular microenvironment acidity of cancer is associated with tumor progression and tumor metastasis (Webb et al., Dysregulated pH: a perfect storm for cancer progression, Nature Reviews. Cancer, 11, p 671, 2011).

Several approaches that aim to utilize this effect of low pH tumor microenvironment to allow targeted delivery of drugs to tumor sites have been explored, including pHLIP peptides (see Andreev, et al., pH-sensitive membrane peptides (pH-LIPs) as a novel class of delivery agents, Mol. Membr. Biol., 27, pp. 341-352, 2010; Adochite et al., Targeting Breast Tumors with pH (Low) Insertion Peptides, Mol. Pharmaceutics, 11 (8), pp 2896-2905, 2014).

Werakkoddy et al., Novel pH-Sensitive Cyclic Peptides, Scientific Reports, 6, 2016, discloses the use of other peptides. Korzeniowska et al., Intracellular pH-sensing using core/shell silica nanoparticles, J Biomed Nanotechnol., 10(7), pp. 1336-45, 2014, discloses the use of nanoparticles. Goa et al., In vivo cancer targeting and imaging with semiconductor quantum dots, Nature Biotechnology, 22 (8), pp. 969-976, 2004, discloses the use of tumor cell-surface marker targeting, etc. The use of such techniques for the imaging of cancer has also been demonstrated, as for example with the pHLIP peptide (see Segala, et al., Accurate analysis of tumor margins using a fluorescent pH Low Insertion Peptide (pHLIP), Int. J. Mol. Sci., 10, pp. 3478-3487, 2009; pHLIP-FIRE, a Cell Insertion-Triggered Fluorescent Probe for Imaging Tumors Demonstrates Targeted Cargo Delivery In Vivo, Karabadzhak et al., ACS Chem. Biol., 9, pp. 2545-2553, 2014). Demoin et al., PET Imaging of Extracellular pH in Tumors with 64Cu- and 18F-Labeled pHLIP Peptides: A Structure-Activity Optimization Study, Bioconjugate Chem., 27 (9), pp 2014-2023, 2016, discloses the use of markers for imaging have included optical fluorescence markers, and PET image contrast enhancement markers. These approaches have also, in part, leveraged pH sensitive dyes, such as Seminaphtharhodafluor (SNARF) dyes (see Tseng et al., In Vivo Fluorescent Labeling of Tumor Cells with the HaloTag® Technology, Current Chemical Genomics, 6, (Suppl 1-M6) pp. 48-54, 2012), that change in their optical emission spectrum depending on the pH of the surrounding media/environment.

As far as physically sensing the pH of the micro-environment, the standard format of a pH glass electrode sensors is large, and only allow single-point pH measurement. While these were used in early studies of tumor cell pH (see Gerweck, L. E., and Seetharaman, K., Cellular pH gradient in tumor versus normal tissue: Potential exploitation for the treatment of cancer, Cancer Res., 1996, 56, 1194-1198), they cannot accurately represent the spatial details of a heterogeneous pH environment typically associated with a tumor micro-environment.

Fiber optic sensor probes of the monitoring of pH, have been developed and commercialized (see Song et al., High-Performance Fiber-Optic pH Microsensors for Practical Physiological Measurements Using a Dual-Emission Sensitive Dye, Anal. Chem., 69 (5), pp 863-867, 1997; Zhou et al., "Multicolored pH-tunable and activatable fluorescence nanoplatform responsive to physiologic pH stimuli," Journal of the American Chemical Society, 134:7803-7811, 2012; Baldini et al: "An extended-range fibre-optic pH sensor", Sensors and Actuators A, 37-38, pp. 180-186, 1993; Lehmann et al: "Fiber-optic pH meter using NIR dye", Sensors and Actuators B 29, pp. 392-400, 1995; and Citterio et al: "Dyes for use in integrated optical sensors", Sensors and Actuators B 38-39, pp. 202-206, 1997, for example).

Figure 2:
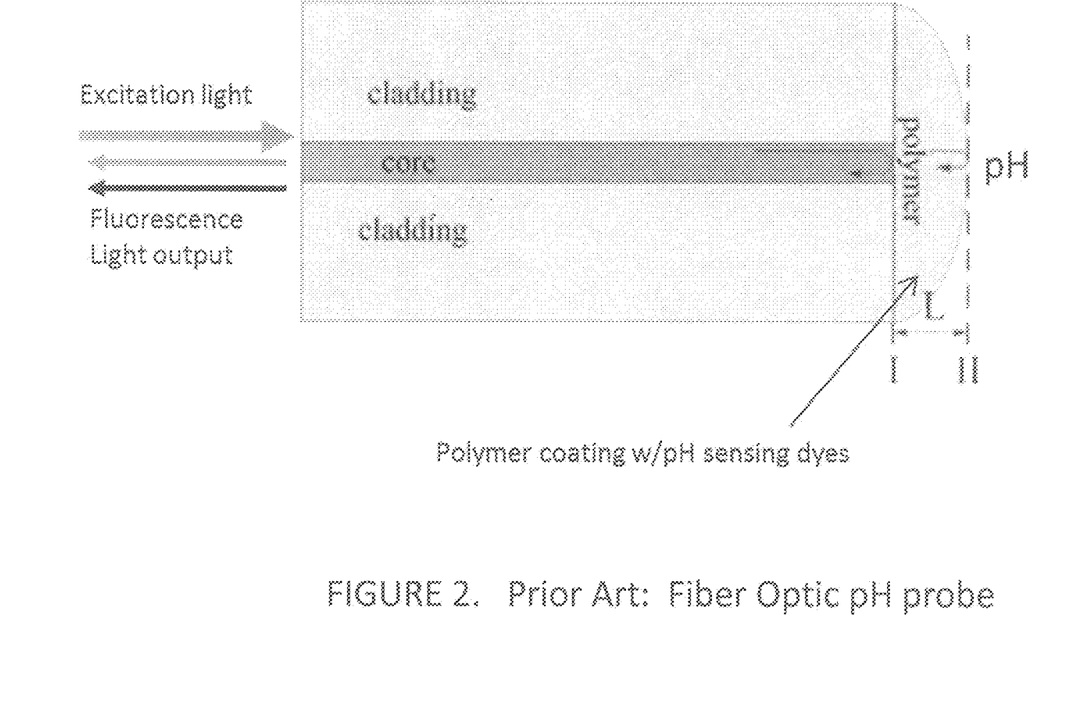
FIG. 2 is a prior art fiber optic pH probe.

FIG. 2 illustrates (prior art) the typical format used, which is an "extrinsic" sensor, where a coating, which itself reacts, or that has compounds/components that react to pH are incorporated on the tip of an optical fiber. These include a variety of fluorophore compounds/molecules, dyes, nanoparticles loaded with dyes etc. This coating provides the 'sensing' layer of the device. Many formats have been published and demonstrated.

The advantage of fiber optic formats for sensing pH include highly localized sensing and fiber tip sizes that provide for high resolution sensing with a 'pixel' size on the order of a typical fiber diameter of nominally 125 μm. This size can be adjusted depending on the need. Optical fiber pH sensors use pH-sensitive dyes encapsulated in a coating applied to the fiber tip: A change in pH triggers a change in absorbance or fluorescence in the coating material that can be detected via an optical source and spectrometer. A good example of a suitable pH-sensing fluorescence dye is the SNARF platform of dyes (see Tseng et al., In Vivo Fluorescent Labeling of Tumor Cells with the HaloTag® Technology, Current Chemical Genomics, 6, (Suppl 1-M6) pp. 48-54, 2012). This dye undergoes a color change in its fluorescence output with pH. In general, the dye is immobilized in a coating that allows interaction with the medium but does not 'bleed out' into sample. Alternatively, the SNARF dyes can be immobilized to nanoparticles which in turn are immobilized to the tip of the fiber probe.

SUMMARY OF THE DISCLOSURE

The present invention is concerned with an apparatus and method for inspecting a biological tissue using a pH-sensitive coating material to determine whether the tissue is normal or cancerous. The coating material is placed in contact to the tissue and excited by an excitation light. The coating material contains one or more pH sensitive dyes arranged to provide a response signal indicative of the pH value of the tissue in response to the excitation. Using a fiber bundle having a plurality of optical fibers forming a linear array or a two-dimensional array adjacent the coating material to capture the response, a pixelated image of localized surface pH in the biological tissue can be achieved. Alternatively, a transparent V-groove block is used to hold a needle biopsy tissue sample, and a coating material provided on the groove walls contacts the tissue sample to sense the pH value of the sample. The response signal from the coating material can be captured by a camera or a fiber bundle for the imaging of the localized surface pH.

Thus, the first aspect of the present invention is apparatus for inspecting a biological tissue, comprising:

an optical medium comprising a coating material arranged to contact the biological tissue, the optical medium arranged to receive an excitation light for providing an optical excitation to the coating material, the coating material having a pH sensitive component configured to provide a response signal indicative of a pH value of the biological tissue in response to the optical excitation; and a display device arranged to present a visual representation of the response signal.

According to an embodiment of the present invention, wherein the optical medium comprises a fiber bundle having a bundle end placed adjacent to the biological tissue, the fiber bundle comprising a plurality of optical fibers, each optical fiber comprising a fiber tip located at the bundle end, the fiber tip having a coating including the coating material, wherein the optical fibers are arranged to receive the excitation light for providing the optical excitation to the coating material, and each of the optical fibers is configured to provide an optical signal indicative of the response signal from the coating material at the fiber tip in response to the excitation, and the visual representation is indicative of the optical signal provided by each of the optical fibers.

According to an embodiment of the present invention, the optical fibers are arranged in a linear array or a two-dimensional array at the bundle end.

According to an embodiment of the present invention, the excitation light has a first wavelength range, and wherein the response signal comprises a wavelength range longer than the first wavelength range, and wherein the visual representation comprises a plurality of pixels, each pixel having a brightness indicative of a spectral value of the optical signal, said apparatus further comprising:

a spectral analyzer arranged to determine the spectral value of the optical signal.

According to an embodiment of the present invention, the apparatus further comprises an optical source for providing the excitation light, wherein each of the optical fibers comprises a first fiber end having the fiber tip and a second fiber end arranged to receive the excitation light.

According to an embodiment of the present invention, the spectral analyzer comprises a spectrometer, the spectrometer arranged to receive the optical signal from each of the optical fibers at the second fiber end.

According to an embodiment of the present invention, the display device is spaced from the spectral analyzer, the spectral analyzer configured to convey information indicative of the brightness of each of pixels to the display device.

According to an embodiment of the present invention, the pH sensitive component comprises one or more pH sensitive dyes.

According to an embodiment of the present invention, the optical medium comprises a V-groove block having a groove arranged to hold a sample of the biological tissue, the V-groove block comprising two groove walls, each groove wall having a coating comprising the coating material, the coating having a first coating side arranged to contact the sample of the biological tissue and an opposing second coating side arranged to receive a fiber bundle, the fiber bundle comprising a plurality of optical fibers, each optical fiber comprising a fiber tip located adjacent to the second coating side of the coating, wherein the optical fibers are arranged to receive the excitation light for providing the optical excitation to the coating material, and each of the optical fibers is configured to provide an optical signal indicative of the response signal from the coating material at the fiber tip in response to the optical excitation, and the visual representation is indicative of the optical signal provided by each of the optical fibers.

According to an embodiment of the present invention, the optical medium comprises a V-groove block having a groove arranged to hold a sample of the biological tissue, the V-groove block comprising two groove walls, each groove wall having a coating comprising the coating material, the coating having a first coating side arranged to contact the sample of the biological tissue and an opposing second coating side, wherein the V-groove block is arranged to receive the excitation light for providing the optical excitation to the coating material from the second coating side, said apparatus further comprising two imaging sensors, each imaging sensor arranged to capture an optical signal from the second coating side indicative of the response signal from the coating material in response to the optical excitation, and the visual representation is indicative of the optical signal captured in each of the imaging sensors.

According to an embodiment of the present invention, the display device comprises a monitor screen or a headset for presenting the visual representation.

According to an embodiment of the present invention, the visual representation of the response signal comprises a pH map overplayed on an image of the biological tissue.

According to an embodiment of the present invention, the optical medium comprises a sensing plate having the coating material and a fiber bundle having a bundle end placed adjacent to the sensing plate, the fiber bundle comprising a plurality of optical fibers, each optical fiber comprising a fiber tip located at the bundle end, wherein the optical fibers are arranged to receive the excitation light for providing the optical excitation to the coating material, and each of the optical fibers is configured to provide an optical signal indicative of the response signal from the coating material in response to the excitation at the fiber tip, and the visual representation is indicative of the optical signal provided by each of the optical fibers.

According to an embodiment of the present invention, the optical medium comprises a sensing plate having the coating material, the sensing plate arranged to receive the excitation light for providing the optical excitation to the coating material, said apparatus further comprising an image sensor configured to capture a spectral image indicative of the response signal from the sensing plate for providing the visual representation to the display device.

The second aspect of the present invention is a method for inspecting a biological tissue, comprising:
arranging an optical medium having a coating material arranged to contact the biological tissue;
receiving an excitation light for providing an optical excitation to the coating material, the coating material comprising a pH sensitive component configured to provide a response signal indicative of a pH value of the biological tissue in response to the optical excitation; and
presenting a visual representation of the response signal.

According to an embodiment of the present invention, the excitation light has a first wavelength range, and the response signal has a wavelength range longer than the first wavelength range, and wherein the visual representation comprises a plurality of pixels, each pixel having a brightness indicative of a spectral value of the response signal, said method further comprising
providing a display device configured to present the visual representation;
determining the spectral value of the response signal; and
conveying information indicative of the spectral value to the display device.

The present invention will become apparent upon reading the description in conjunction with FIGS. 3 to 7.

DETAILED DESCRIPTION OF THE INVENTION

The present invention makes use of a bundled fiber-optic probe for the imaging of localized surface pH in a biological tissue and specifically for the determination of tumor margin or the boundary between normal and cancerous cells. The approach also provides direct mapping of the tumor margin via a display that could be provided for a surgeon's or pathologist's inspection, or via a display mapped back onto the probe via a second fiber optic bundle that allows the surgeon to see the pH map as soon as the probe is contacted with the tissue surface. FIGS. 3 to 7 show some representative examples of the present invention.

Figure 3:
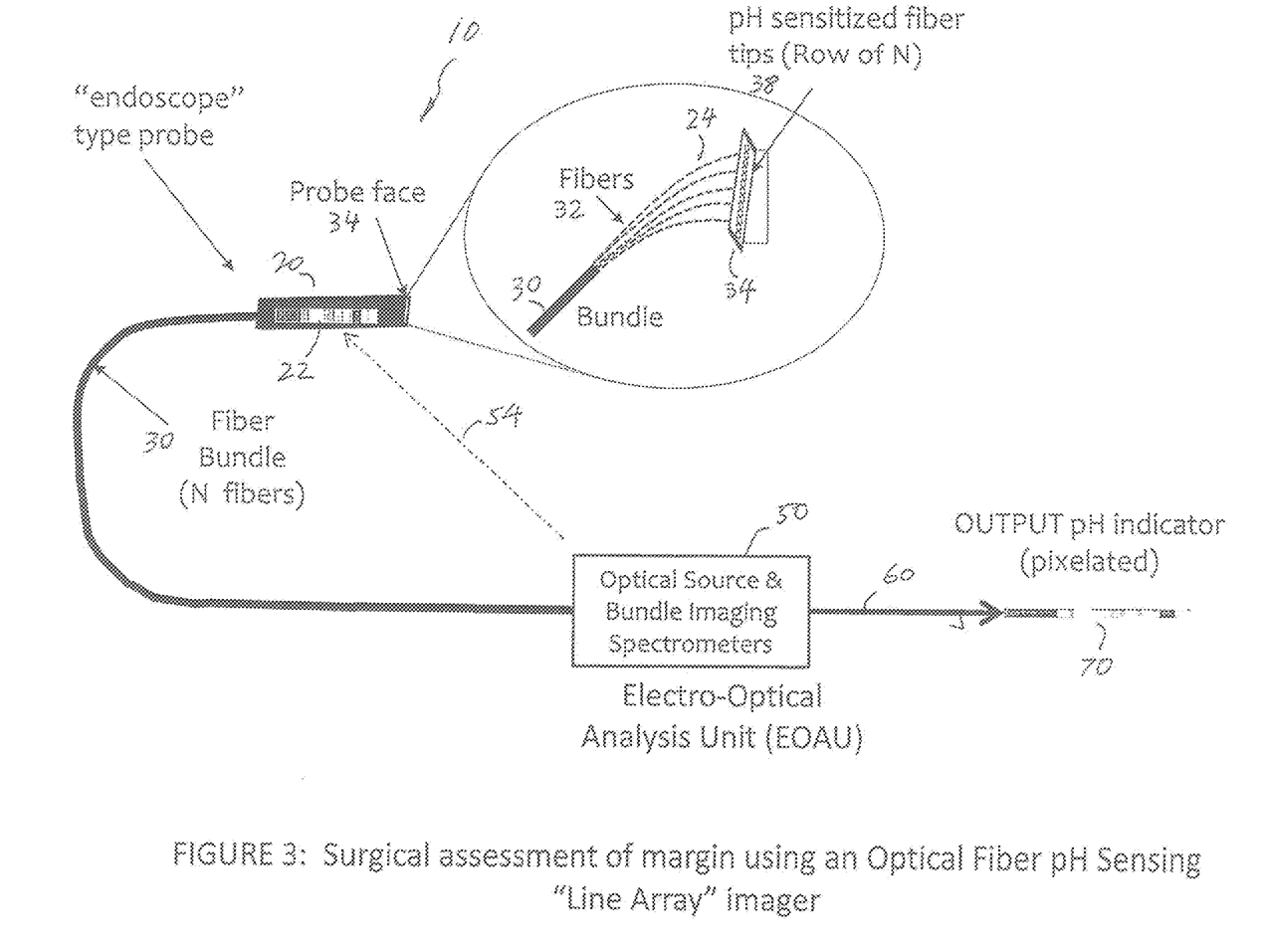
FIG. 3 illustrates an apparatus for inspecting a biological tissue, according to an embodiment of the present invention, wherein the optical fiber tips are arranged in a linear array.

FIG. 3 illustrates an apparatus for inspecting a biological tissue, according to an embodiment of the present invention. The apparatus is illustrated as a 'line array' imager embodiment where fiber optic tip probes sensitized to local pH are arranged to allow visualization of the tumor margin, e.g., the transition from tumor to normal tissue. As an example, the "line array" here could be on the order of 0.25 mm×5 mm in length depending on the number of fibers used. The system output is fed to a display unit in the electro-optical analysis unit (EOAU), or to some form of external display to present a visual mapping of the pH value of the biological tissue. Alternatively, feedback is provided to a small LED display, or other display in suitable electronic format, built into the probe structure, for example, into the handle as indicated by the dashed line, to provide a direct visual feedback to the surgeon. This type of probe may be used to sample areas of a cancerous lesion where the surgeon is uncertain about the location of the margin from a direct inspection of the cellular/morphological structure.

As shown in FIG. 3, an apparatus 10 comprises a fiber bundle 30 having a plurality of optical fibers 32 (N fibers arranged in a linear array) forming an "endoscope" type probe 20 with a probe face 34 at the bundle end 24 to be placed adjacent to a sample area of a cancerous lesion, for example. Each of the optical fibers 32 has a fiber tip 38 located at the bundle end 24 and each of the fiber tips 38 has a coating arranged to contact the sample area. The apparatus 10 has an electro-optical analysis unit (EOAU) 50, which has an optical source to provide an excitation light for providing an excitation to the coating material which contains one or more pH sensitive dyes. A change in pH would trigger a change in absorbance or fluorescence in the coating material. For example, the dyes may undergo a color change in the fluorescence output in response to the pH. In response to the excitation, each of the optical fibers is configured to provide a signal from the coating indicative of a pH value of the sample area at the fiber tip. The EOAU 50 may have a bundle imaging spectrometric unit configured to analyze the signals from the optical fibers 32. The system output 60 from the spectrometric unit may be arranged as a pixeled pH indicator 70. The apparatus 10 may have a display device 22 on the probe 20 arranged to present a visual representation of the signal provided by each of the optical fibers based on information 54 conveyed from the EOAU 50.

Figure 3A:
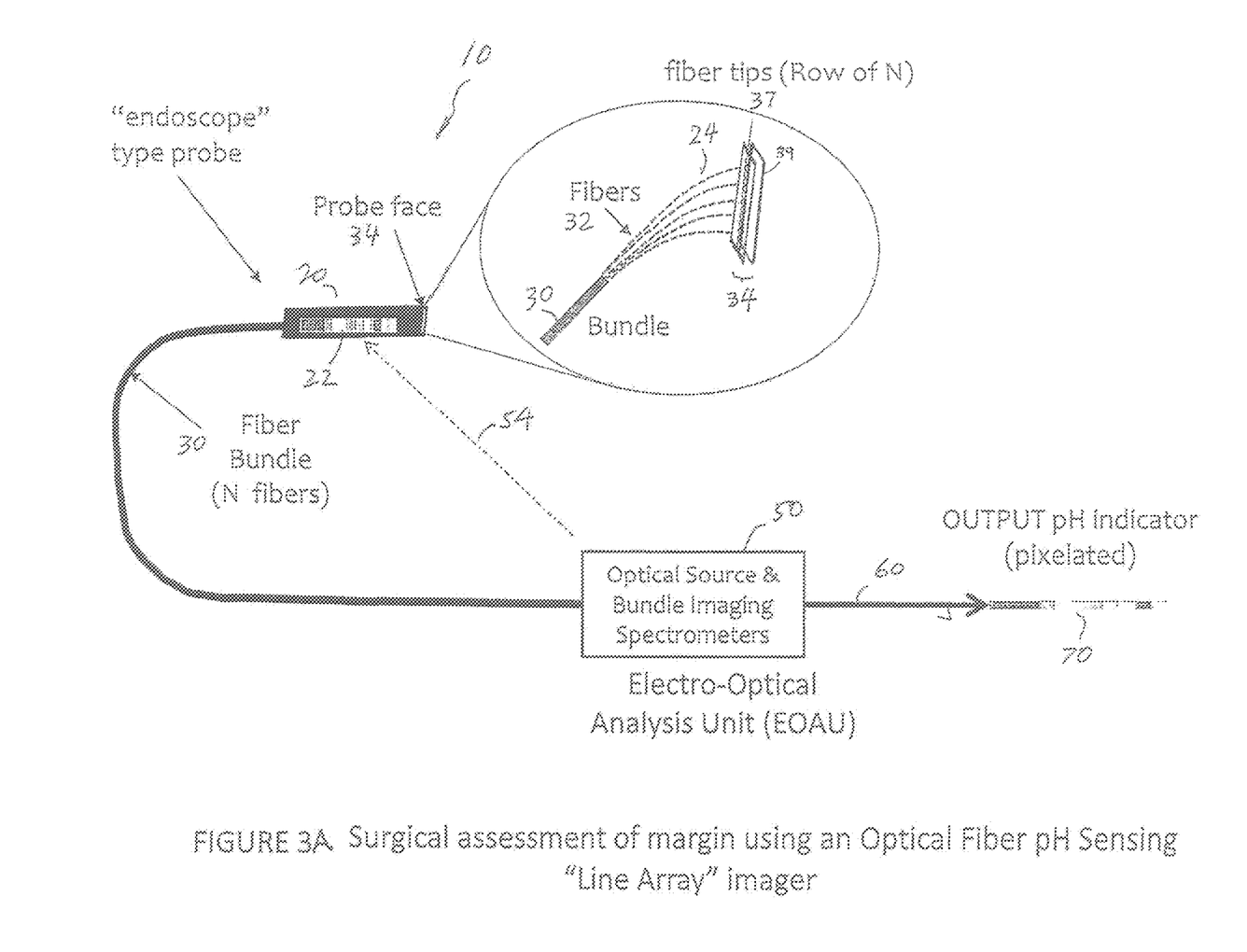
FIG. 3A illustrates a different embodiment of the apparatus of FIG. 3.

In the embodiment as shown in FIG. 3A, the probe face 34 comprises a sensing plate 39 having a pH sensitive coating arranged to contact a sample area of a cancerous lesion, and a fiber bundle 30 having a plurality of optical fibers 32 (N fibers arranged in a linear array) forming an "endoscope" type probe 20 with the probe face 34 at the bundle end 24. Each of the optical fibers 32 has a fiber tip 37 located at the bundle end 24 to be placed adjacent to the sensing plate 39. The optical fibers 32 are arranged to receive the excitation light for providing the optical excitation to the coating and each of the optical fibers 32 is arranged to provide an optical signal indicative of the response signal from the pH-sensitive coating in response to the excitation near the fiber tip 37. The sensing plate 39 can be separate from the fiber tips 37 or be bonded or attached to the fiber tips 37.

Figure 4:
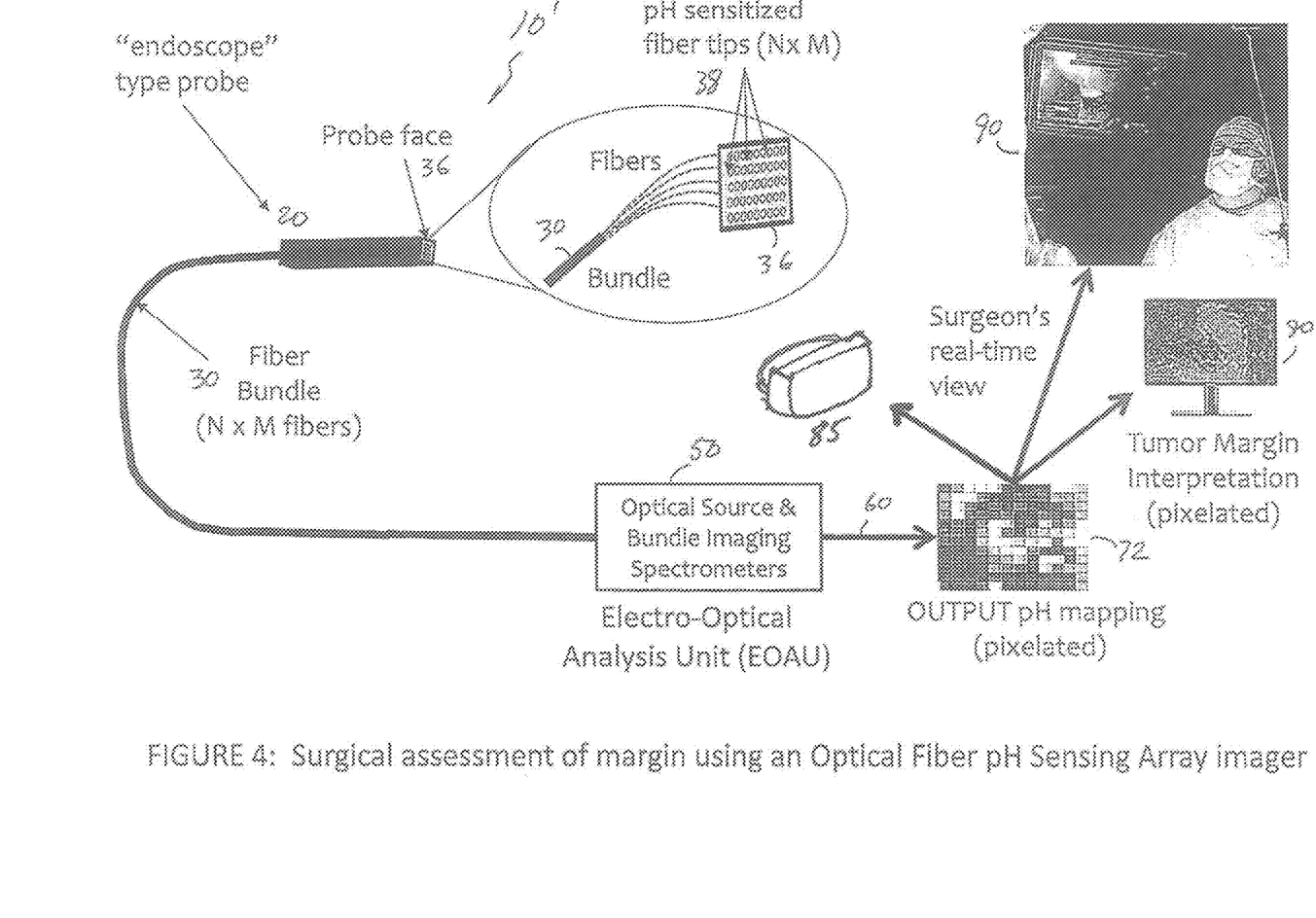
FIG. 4 illustrates an apparatus for inspecting a biological tissue, according to an embodiment of the present invention, wherein the optical fiber tips are arranged in a two-dimensional array.

As a different embodiment, FIG. 4 depicts a 2D array of fiber probes that sense over a certain area to provide an "areal" depiction of the margin. As an example, the "2D array" here could be on the order of 5 mm×5 mm, or 10 mm×10 mm depending on the number of fibers used. The image "spatial resolution" produced is defined by the total number of fibers. For a fiber diameter of nominally 125 μm, a 50×50 fiber array would have a probe size of ~6.25 mm×6.25 mm and 2500 'pixels'. This might prove more valuable to a surgeon in the case where the margin has more detailed structural changes. As in the previous embodiment, the output of the system could be displayed on a screen on the EOAU, or on an external display.

As shown in FIG. 4, the apparatus 10' comprises a fiber bundle 30 having a plurality of optical fibers 32 (N×M fibers arranged in a two-dimensional array) forming an "endoscope" type probe 20 having a probe face 36 at the bundle end 26 to be placed adjacent to a sample area of a cancerous lesion, for example. Each of the optical fibers 32 has a fiber tip 38 located at the bundle end 26 and each of the fiber tips 38 has a coating arranged to contact the sample area. The apparatus 10' has an electro-optical analysis unit (EOAU) 50 with an optical source to produce an excitation light for providing an excitation to the coating material which contains one or more pH sensitive dyes. In response to the excitation, each of the optical fibers is configured to provide a signal from the coating indicative of a pH value of the sample area at the fiber tip. The EOAU 50 may have a bundle imaging spectrometric unit configured to analyze the signals from the optical fibers 32. The system output 60 from the spectrometric unit in the EOAU 50 is arranged into pixelated pH mapping 72. According to an embodiment of the present invention, image data from the pixeled pH mapping 72 can be conveyed to a display device 80 for presenting a visual representation of the tumor margin, for example. The image data from pixelated pH mapping 72 can also be conveyed to a display system 90 in real-time to allow a surgeon to view the tumor margin.

The pixelated pH mapping 72 can also be conveyed to a headset 85 which can be a form of VR (virtual reality) headset or AR (augmented reality) headset or glasses. The pH mapping 72 can be overplayed on a direct view such as a heads-up display.

Figure 4A:
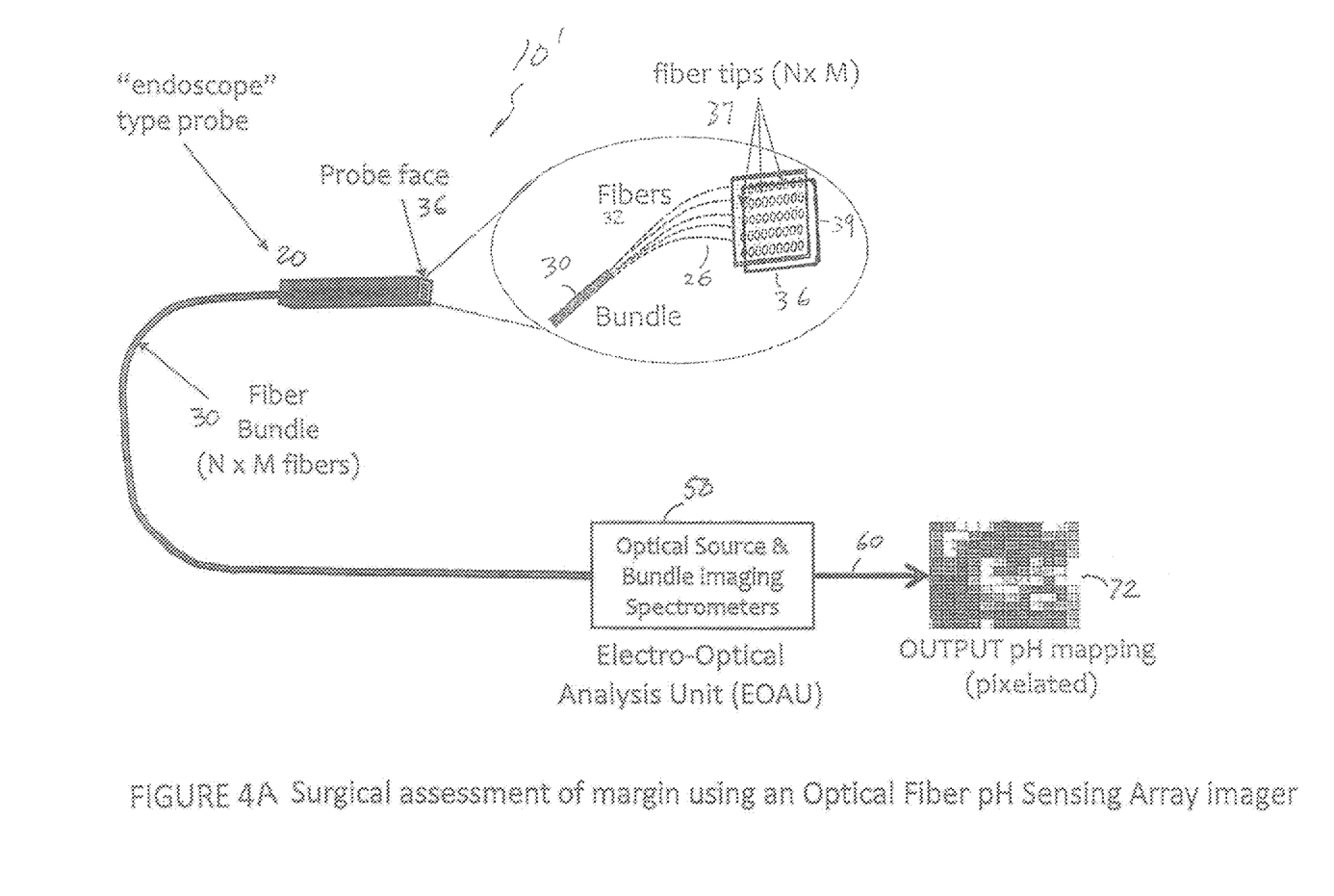
FIG. 4A illustrates a different embodiment of the apparatus of FIG. 4.

In the embodiment as shown in FIG. 4A, the probe face 36 comprises a sensing plate 39 having a pH sensitive coating arranged to contact a sample area of a cancerous lesion, and a fiber bundle 30 having a plurality of optical fibers 32 (N×M fibers arranged in a two-dimensional array) forming an "endoscope" type probe 20 with the probe face 36 at the bundle end 26. Each of the optical fibers 32 has a fiber tip 37 located at the bundle end 26 to be placed adjacent to the sensing plate 39. The optical fibers 32 are arranged to receive the excitation light for providing the optical excitation to the coating and each of the optical fibers 32 is arranged to provide an optical signal indicative of the response signal from the pH-sensitive coating in response to the excitation near the fiber tip 37. The sensing plate 39 can be separate from the fiber tips 37 or can be bonded or attached to the fiber tips 37.

Figure 4B:
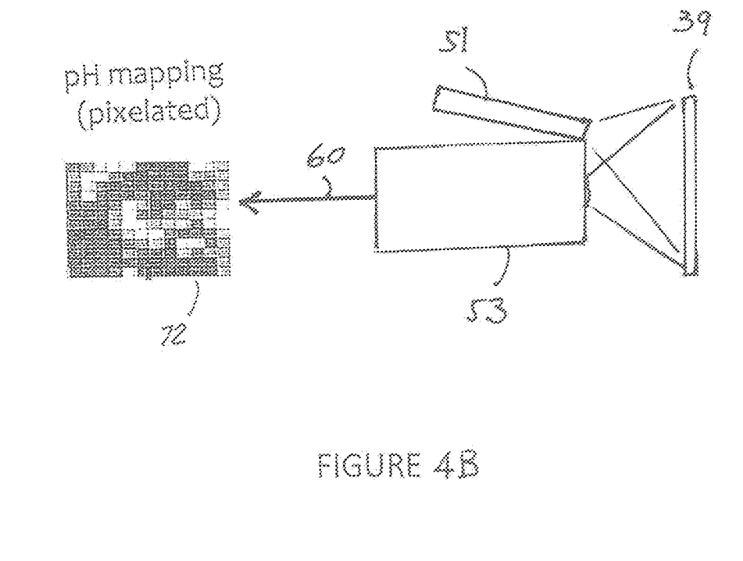
FIG. 4B illustrates yet another embodiment of the apparatus wherein an imaging device is used to capture the response from a sensing plate.

In the embodiment as shown in FIG. 4B, a sensing plate 39 having a pH sensitive coating arranged to contact a sample area of a cancerous lesion, and an optical source 51 such as a short wavelength laser is used to provide the optical excitation to the coating. An imaging sensor or imaging system 53 is placed near the sensing plate 39 to capture a spectral image indicative of the response signal from the sensing plate 39 for providing the visual representation of the pH mapping 72. The imaging system 53 can be a CCD array with wavelength selective filters or a "hyperspectral" image device.

Figure 5:
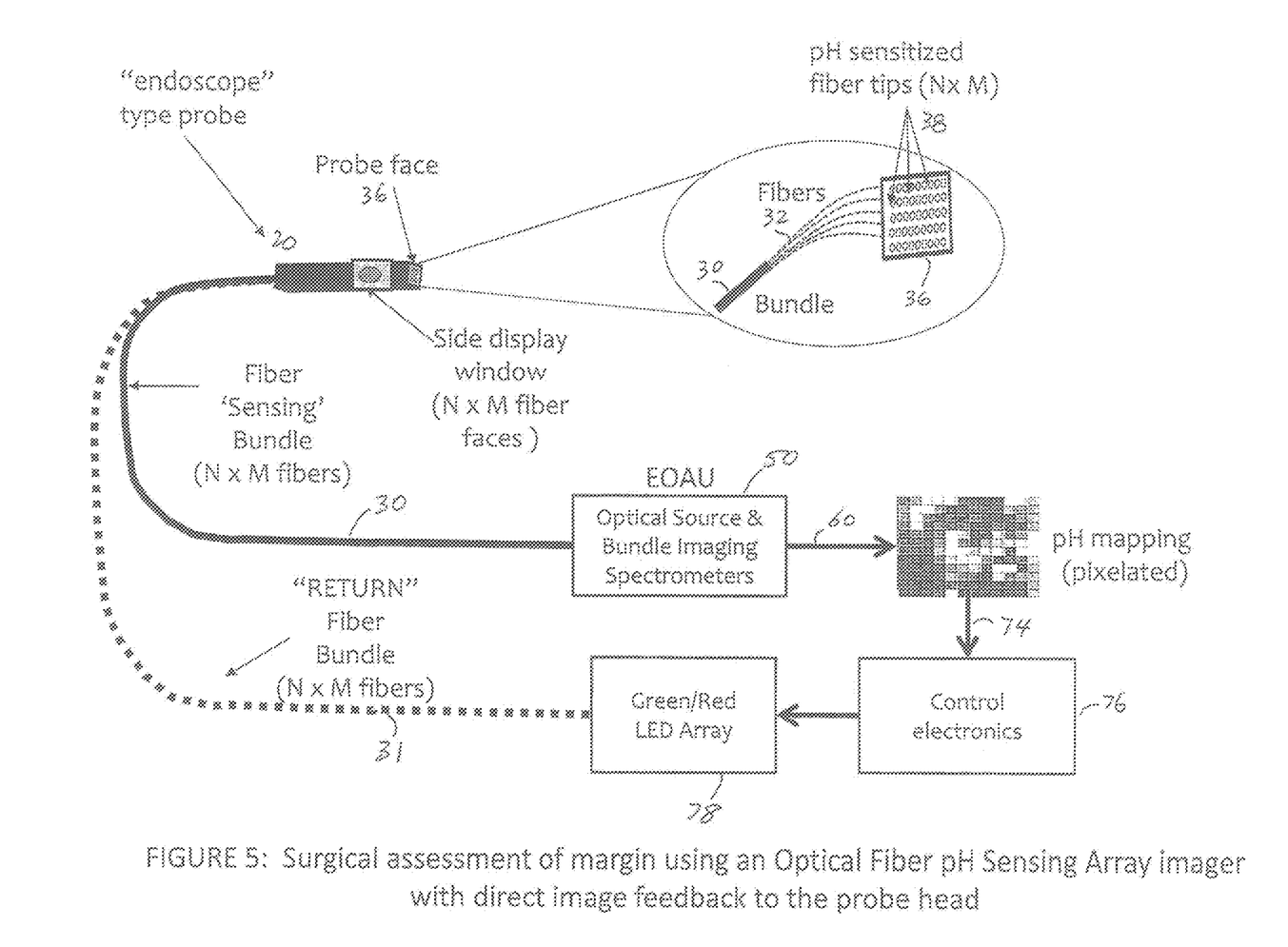
FIG. 5 illustrates an apparatus for inspecting a biological tissue, according to an embodiment of the present invention, wherein a direct image feedback is used for displaying an image near the probe head.

FIG. 5 shows a different version of the 2D probe, where the output is displayed directly alongside the probe tip by using a secondary 'return' fiber bundle to convey the analyzed surface tissue pH states into a simple two-color, or multi-color (e.g., red and green as examples) display. Here, the optical signal returned from each fiber pH probe tip in the 2D sensing head is detected and converted into a spectral value indicative of the PH value. This spectral value is then sent to an electronic controller that controls the intensity of a dual color LED unit (for example, Green and Red) such that the LED emits green light for a pH above 7.0, with the intensity/brightness increasing with pH up to a value of 7.6, and the LED emits red light for a pH below 7.0, with intensity/brightness increasing with lowering pH value down to a pH of 6.4. This "on-probe" display may be angled to provide the surgeon with optimal visibility of the system output while positioning the probe onto tissue areas of interest for margin evaluation.

It should be noted that the upper and lower limits of pH defined in the above are nominal and others could be defined, but these represent the physiological pH values of interest generally for the pH of the microenvironment of cancer tissue.

As shown in FIG. 5, the pixelated pH mapping 72 is conveyed as imaging data 74 to a control electronics unit 76 which controls the intensity of a dual wavelength LED array 78. For example, the LED array 78 comprises green and red LEDs that emit green light for a pH above 7.0 and red light for a pH below 7.0. The light emitted by the LED array 78 is conveyed to a side display window 23 on the probe 20 via a "return" fiber bundle (N×M fibers) 31. The side display window 23 is formed from N×M fiber tips, for example.

Figure 7:
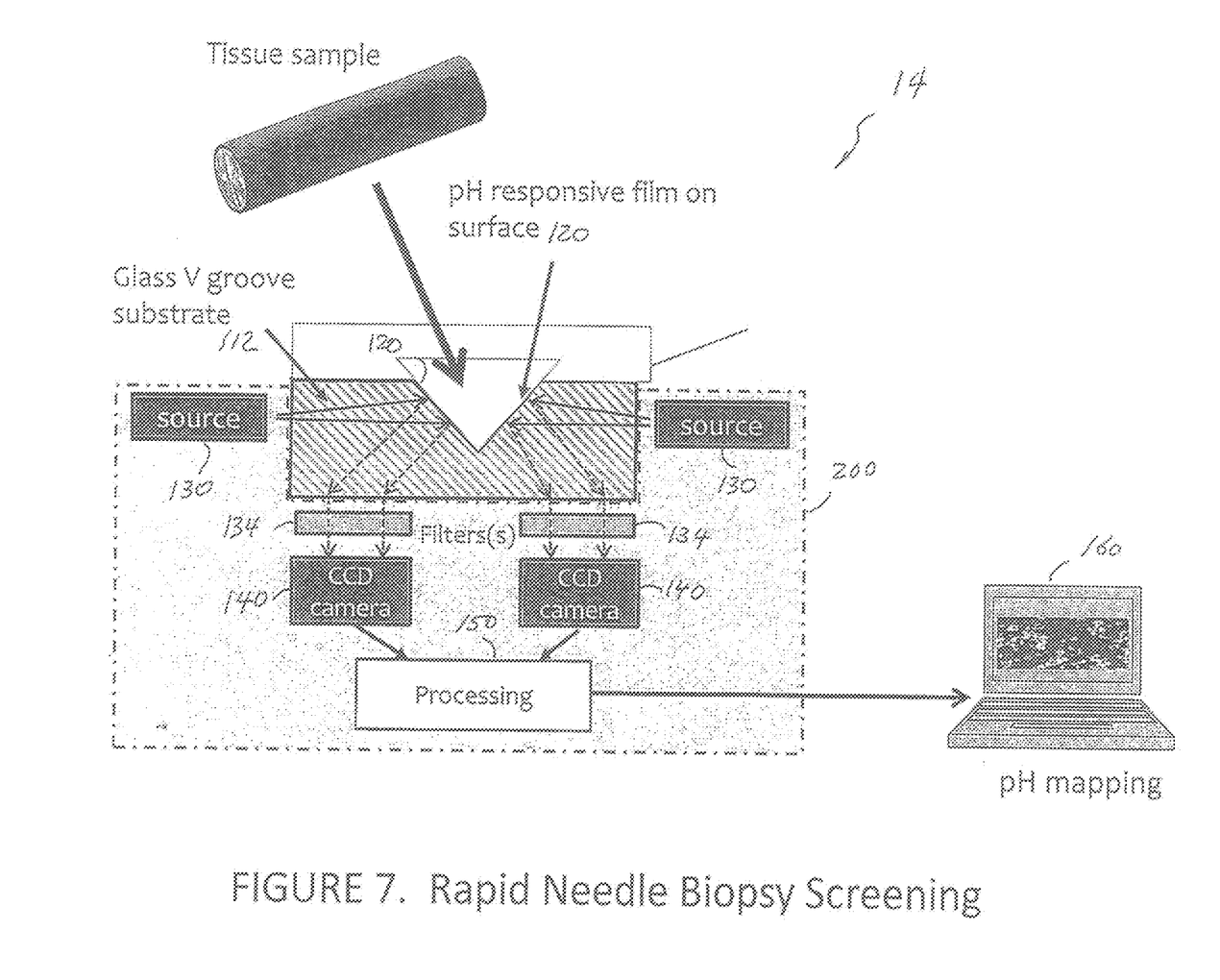
FIG. 7 illustrates an apparatus for inspecting a needle biopsy tissue sample, according to an embodiment of the present invention, wherein cameras are used to capture the response of pH responsive films.

The advantage of the optical feedback/visual mapping to the probe head as described in FIGS. 5 and 7 is that the probe with a visual display contains no electronics and is completely electrically passive: this is an advantage of sensing in surgical procedures as it eliminates the risk of electrical shock/electrical interference etc.

Alternative Embodiments/Utility

1) EXCISED TUMOR PROFILING:

Once a surgeon has completed a surgical excision of a tumor, the tumor is marked and tagged for areas of concern where the margin may not have been fully encompassed/captured surgically. Tissue samples taken from the locations are then sent to pathology for margin determination. This is a very time-consuming process, as for a giving tumor, there could be tens of samples taken, each of which must be dissected, fixed, and cut into very thin slices, which are then stained for contrast and mounted onto glass slides. The slides are examined by a pathologist under a microscope for verification that the surgical margin was achieved all around the 3D edges of the tumor. The probe that senses the pH level of the biological tissue as described in the present invention can also be used in this application to quickly validate areas of the excised tumor that have normal tissue on the surface and those that potentially have tumor cells on the surface, indicating the margin was not removed in the surgery.

2) BIOPSY SCREENER:

Standard histopathology of biopsy specimens is slow and labor-intensive. Several tissue samples are often harvested from a patient to ensure the probably that a good sample of tumor tissue is being sent on to pathology for analysis. As there is not a priori indication of which samples may contain tumor samples, all samples must be processed. The negative/clear read rate of these samples is much greater than the positive read rate. Consequently, a device that could screen the sample prior to their full pathology processing could be a significant advantage, as it reduces the work load for pathology departments by providing pre-screened samples.

Figure 6:
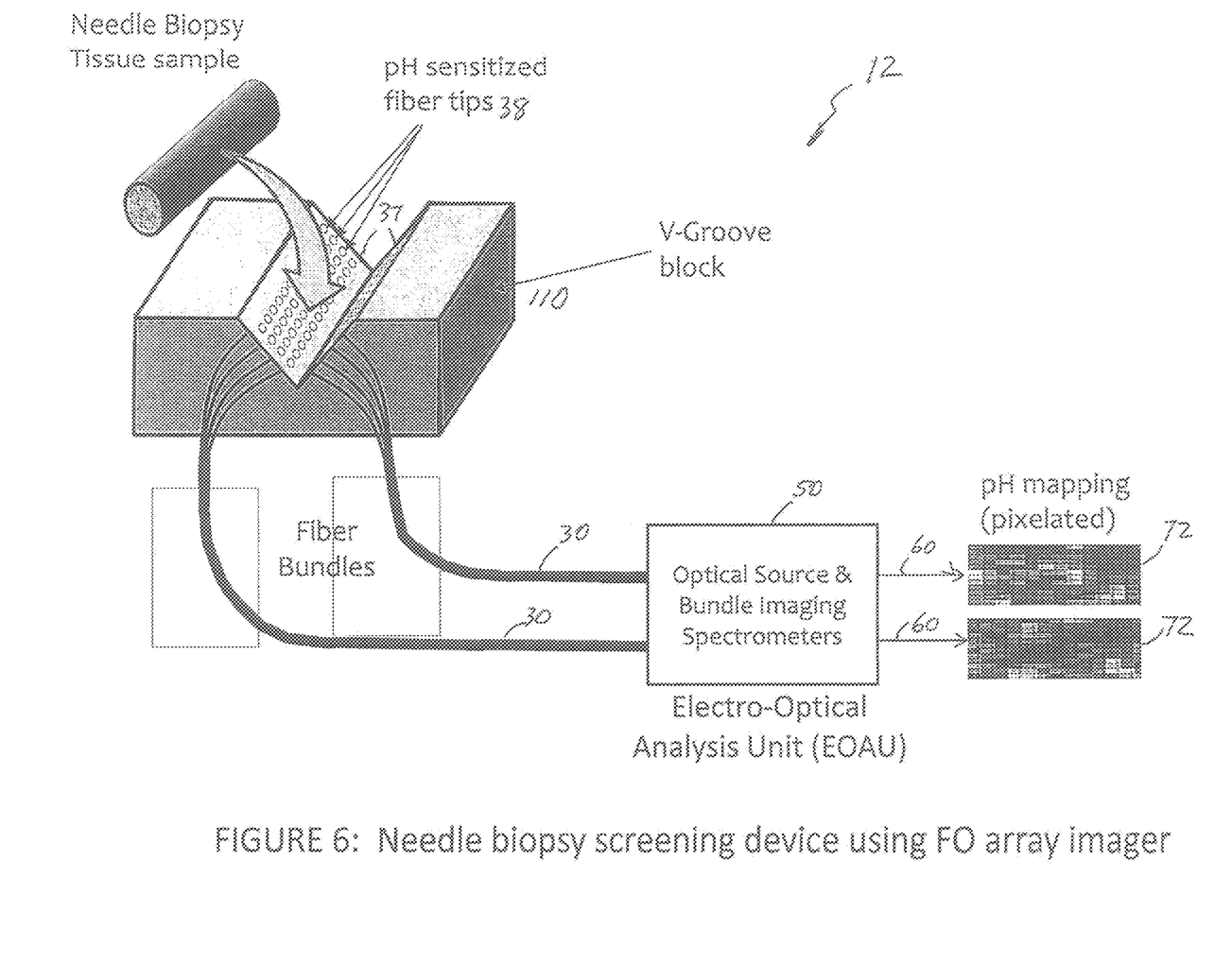
FIG. 6 illustrates an apparatus for inspecting a needle biopsy tissue sample, according to an embodiment of the present invention, wherein the sample is held in the groove of a V-groove block and optical fiber tips are arranged on the surfaces of the groove walls to collect the response signal.

FIG. 6 illustrates a format of the pH array sensing head configured into a V-groove tissue sample holder. This type of device would provide a very rapid test of pH in samples recovered from biopsy procedures and ensure that samples forward for further evaluation contain cancerous tissue. As shown in FIG. 6, the apparatus 12 comprises a V-groove block 110 having a V-groove to hold a tissue sample 100. Each of the two groove walls forming the V-groove is used as a probe face 37 with pH sensitized fiber tips 38. As with the embodiment as shown in FIG. 4, the EOAU 50 is arranged to provide an excitation light via two fiber bundles 30 to excite a pH-sensitized coating on each of the probe faces 37. The bundle imaging spectrometric unit in the EOAU 50 is configured to analyze the signals from the probe faces 37. The system output 60 from the spectrometric unit is arranged into pixelated pH mapping 72.

FIG. 7 illustrates an additional embodiment of the present invention using a simple imaging system and a pH responsive film attached to the surface of the V grooves. In this embodiment, imaging of the segments of the pH responsive film can be realized with a simple imaging device, such as a CCD chip or small camera etc. Once the tissue is in contact with the pH responsive film, the tissue pH affects the fluorescence of the film allowing the pH of the tissue to be mapped. Thus, the presence of cancerous tissue can be detected. Here, the V-groove section with pH sensitized coatings can be a disposable component that is located/positioned into an instrumentation module which may comprise the sensing/imaging system optics and electronics. The use of a disposable V-groove sample holder element could prevent cross-contamination of the pH sensitive surfaces from sample to sample.

As shown in FIG. 7, the apparatus 14 comprises an optically transparent V-groove block 112 having a V-groove to hold a tissue sample 100. Each of the two surfaces or groove walls of the V-groove has a pH responsive film 120. Each of the optical sources 130 is used to provide an excitation light to excite the pH responsive film 120. The fluorescence from each of the pH responsive films 120 is directed to a CCD camera 140 via a filter 134. The captured fluorescence, after being processed by a processor 150, is presented as pH mapping on a display device 160. The optically transparent V-groove block 112, the optical sources, the filters 134, the CCD cameras 120 and the processor 150 can all be arranged in an instrumentation module 200.

In summary, the present invention uses two versions of optical media to inspect a biological tissue: a fiber bundle having a plurality of optical fibers to be placed adjacent to the biological tissue, and an optically transparent V-groove block having a groove to hold a sample of the biological tissue. Each of the optical media comprises a coating material arranged to contact the biological tissue. The optical medium is arranged to receive an excitation light for providing an optical excitation to the coating material. The coating material contains a pH sensitive or responsive component configured to provide a response signal indicative of a pH value of the biological tissue in response to the optical excitation. A display device is arranged to present a visual representation of the response signal.

The Scope of the Invention

Thus, although the present invention has been described with respect to one or more embodiments thereof, it will be understood by those skilled in the art that the foregoing and various other changes, omissions and deviations in the form and detail thereof may be made without departing from the scope of this invention.

What is claimed is:

1. A screening device for inspecting a sample of biological tissue, comprising:
   a V-groove block having a groove configured to hold a sample of biological tissue, the groove having at least one groove wall with a pH sensitive surface that has a pH responsive film attached thereto and configured to form a probe face, contact the sample of biological tissue, receive excitation light that excited the pH responsive film and provide a response signal containing information about a pH value of the sample of biological tissue in contact with the pH responsive film; and
   an indication device configured to receive the response signal, and provide an indication of the pH value of the sample of biological tissue in contact with the pH responsive film.

2. A screening device according to claim 1, wherein the screening device comprises an electro-optical analysis unit having an optical source and fiber bundle imaging spectrometer configured to provide the excitation light, receive the response signal, and provide imaging spectrometer signaling containing information about a spectrometer image of the response signal.

3. A screening device according to claim 2, wherein the optical source and fiber bundle imaging spectrometer comprises a first fiber bundle configured to provide the excitation light to the pH sensitive surface, and a second fiber bundle configure to receive the response signal.

4. A screening device according to claim 1, wherein
   the screening device comprises fiber bundles;
   the groove wall is configured to receive the fiber bundles; and
   the pH sensitive surface comprises a pH responsive film.

5. A screening device according to claim 4, wherein the pH responsive film is configured to form the probe face, contact the sample of biological tissue, receive the excitation light and provide the response signal containing information about the pH value of the sample of biological tissue in contact with the pH sensitive surface.

6. A screening device according to claim 5, wherein the screening device comprises at least one optical source configured to provide the excitation light to excite the pH sensitive surface.

7. A screening device according to claim 6, wherein the screening device comprises:
   at least one filter configured to receive the response signal, and provide a filtered response signal containing information about a filtered response; and
   at least one CCD camera configured to receive the filtered response signal, and provide at least one CCD camera signaling containing information about filtered and CCD camera response signaling sensed.

8. A screening device according to claim 7, wherein the screening device comprises a processing module configured to receive the at least one CCD camera signaling, and provide processed CCD camera and pH mapping signaling for displaying on a display device.

9. A screening device according to claim 7, wherein the screening device comprises the display device configured to receive the processed CCD camera and pH mapping signaling and display the PH mapping containing indication of the pH value of the sample of biological tissue in contact with the respective pH sensitive surface.

10. A screening device according to claim 1, wherein the V-groove block comprises a transparent V groove substrate.

11. A screening device according to claim 10, wherein the transparent V groove substrate is a glass V groove substrate.

12. A screening device according to claim 10, wherein the transparent V groove substrate includes the groove having the at least one groove wall with the pH sensitive surface comprising a pH responsive film.

13. A screening device according to claim 12, wherein the pH responsive film is configured to form the probe face, contact the sample of biological tissue, receive the excitation light and provide the response signal containing information about the pH value of the sample of biological tissue in contact with the pH sensitive surface.

14. A screening device according to claim 1, wherein the pH sensitive surface comprises one or more pH sensitive dyes.

15. A screening device according to claim 1, wherein the pH sensitive surface comprises one or more Raman dyes responsive to a pH.

16. A screening device according to claim 1, wherein the pH sensitive surface comprises one or more pH sensitive dyes used in combination with one or more Raman dyes responsive to pH.

17. A screening device for inspecting a sample of biological tissue, comprising:
   a V-groove block having a groove configured to hold a sample of biological tissue, the groove having at least one groove wall with a pH sensitive surface configured to form a probe face, contact the sample of biological tissue, receive excitation light and provide a response signal containing information about a pH value of the sample of biological tissue in contact with the pH sensitive surface;
   an indication device configured to receive the response signal, and provide an indication of the pH value of the sample of biological tissue in contact with the pH sensitive surface; and
   fiber bundles having pH sensitive tips with pH sensitive surfaces; and
   the at least one groove wall being configured to receive the pH sensitive tips with the pH sensitive surfaces so as to contact the sample of biological tissue.

18. A screening device according to claim 17, wherein the at least one groove wall comprises two V-shaped groove walls, each V-shaped groove wall having the pH sensitive surface configured to form the probe face, contact the sample of biological tissue, receive the excitation light and provide the response signal containing information about the pH value of the sample of biological tissue in contact with the pH sensitive surface.

19. A screening device for inspecting a sample of biological tissue, comprising:
   a V-groove block having a groove configured to hold a sample of biological tissue, the groove having at least one groove wall with a pH sensitive surface configured to form a probe face, contact the sample of biological tissue, receive excitation light and provide a response signal containing information about a pH value of the sample of biological tissue in contact with the pH sensitive surface;
   an indication device configured to receive the response signal, and provide an indication of the pH value of the sample of biological tissue in contact with the pH sensitive surface;
   an electro-optical analysis unit having an optical source and fiber bundle imaging spectrometer configured to provide the excitation light, receive the response signal, and provide imaging spectrometer signaling containing information about a spectrometer image of the response signal; and a pH mapping device configured to receive the imaging spectrometer signaling, and provide pH mapping pixelated device signaling containing the indication of the pH value of the sample of biological tissue in contact with the respective pH sensitive surface.

20. A screening device for inspecting a sample of biological tissue, comprising:

a V-groove block having a groove configured to hold a sample of biological tissue, the groove having at least one groove wall with a pH sensitive surface configured to form a probe face, contact the sample of biological tissue, receive excitation light and provide a response signal containing information about a pH value of the sample of biological tissue in contact with the pH sensitive surface;

an indication device configured to receive the response signal, and provide an indication of the pH value of the sample of biological tissue in contact with the pH sensitive surface;

an electro-optical analysis unit having an optical source and fiber bundle imaging spectrometer configured to provide the excitation light, receive the response signal, and provide imaging spectrometer signaling containing information about a spectrometer image of the response signal; and the optical source and fiber bundle imaging spectrometer having an imaging spectrometer element, including a hyperspectral imager, the image spectrometer element being arranged to receive the response signal from the pH sensitive surface in response to the excitation light provided on the sample of the biological biopsy tissue.

21. A screening device for inspecting a sample of biological tissue, comprising:

a V-groove block having a groove configured to hold a sample of biological tissue, the groove having at least one groove wall with a pH sensitive surface configured to form a probe face, contact the sample of biological tissue, receive excitation light and provide a response signal containing information about a pH value of the sample of biological tissue in contact with the pH sensitive surface; and an indication device configured to receive the response signal, and provide an indication of the pH value of the sample of biological tissue in contact with the pH sensitive surface, the indication device having a monitor screen or a headset for providing a visual representation of the pH value of the sample of biological tissue in contact with the respective pH sensitive surface, the visual representation of the response signal having an interpretation of a pH map into a cancer tissue presence (%), overplayed on a direct image of the sample of the biological biopsy tissue sample.

* * * * *